United States Patent [19]

Arrington

[11] 4,306,805
[45] Dec. 22, 1981

[54] REFRACTOMETRIC DEVICE

[76] Inventor: James R. Arrington, S. 10630 W. 203 North Shore Dr., Muskego, Wis. 53150

[21] Appl. No.: 45,560

[22] Filed: Jun. 4, 1979

[51] Int. Cl.³ .............................................. G01N 21/43
[52] U.S. Cl. ..................................... 356/133; 356/136
[58] Field of Search ........................ 356/133, 135, 136

[56] References Cited

U.S. PATENT DOCUMENTS

| | | | |
|---|---|---|---|
| 3,282,149 | 11/1966 | Shaw et al. | 356/133 |
| 3,299,770 | 1/1967 | Witt et al. | 356/133 |
| 3,850,528 | 11/1974 | DeBellis | 356/133 |
| 3,977,790 | 8/1976 | Schweizer | 356/136 |
| 4,187,025 | 2/1980 | Harmer | 356/133 |

FOREIGN PATENT DOCUMENTS 2137842  2/1973  Fed. Rep. of Germany ...... 356/133

*Primary Examiner*—R. A. Rosenberger
*Attorney, Agent, or Firm*—Michael, Best & Friedrich

[57] ABSTRACT

An immersion-type refractometric device for measuring the concentration of solutions including a probe having a curved measuring surface on the immersible tip. A light source directs a diverging light beam internally through the probe body toward the measuring surface. In one embodiment, light reflected from the measuring surface is received by a light-reflecting surface on the probe tip and directed through the probe body toward a photosensitive element connected to a measuring circuit which provides an output signal indicative of solution concentration. In another embodiment, the photosensitive element is located in the probe tip and receives reflected light directly from the measuring surface. When a linear output is desired over a range of solution concentrations, the measuring surface is curved to produce incidence angles of the reflected light varying from a minimum corresponding to the critical angle when the solution concentration is at the lower limit of the predetermined range to a maximum corresponding to about 1.25 times the critical angle when the solution concentration is at the upper limit of the predetermined range. When a switching function is desired, the curvature of the measuring surface is contoured so that the incidence angles are substantially constant across the measuring surface.

7 Claims, 9 Drawing Figures

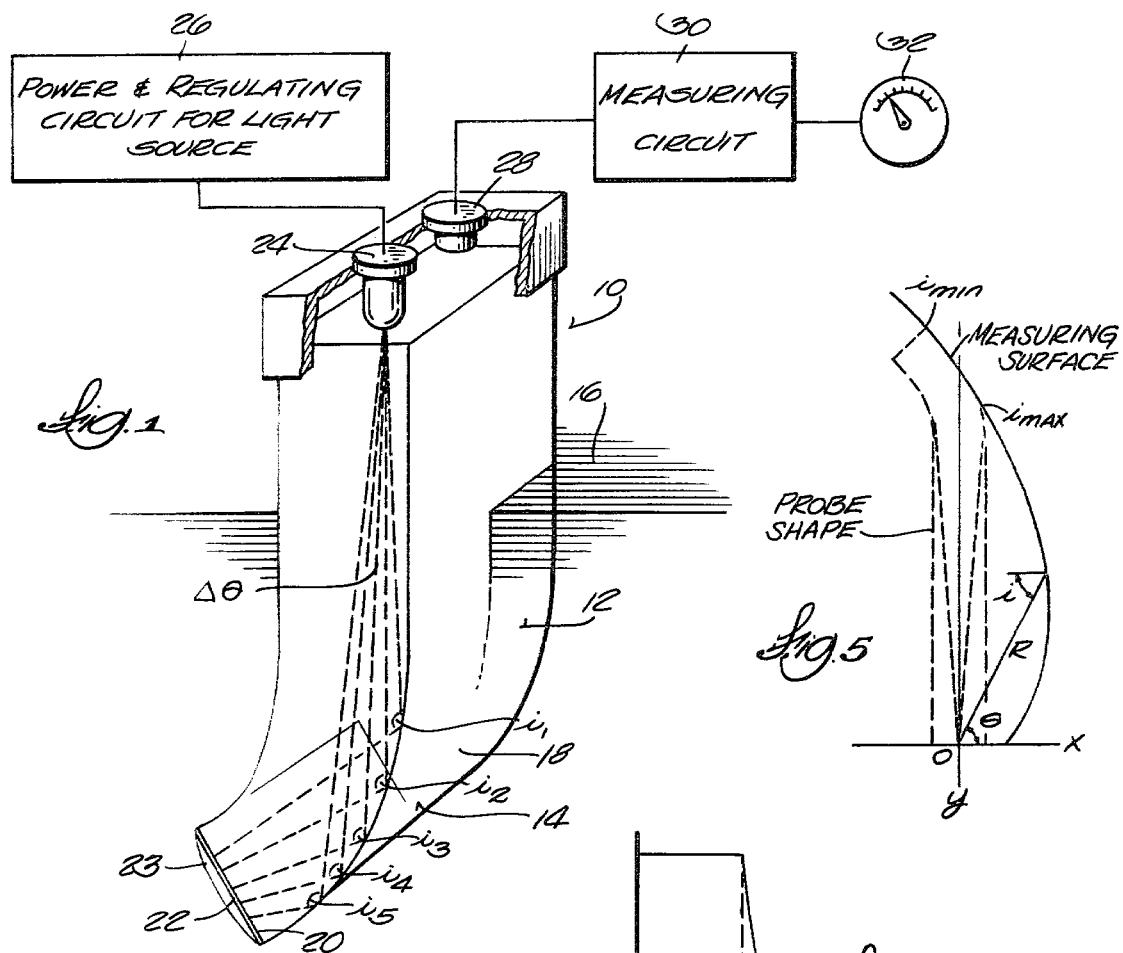

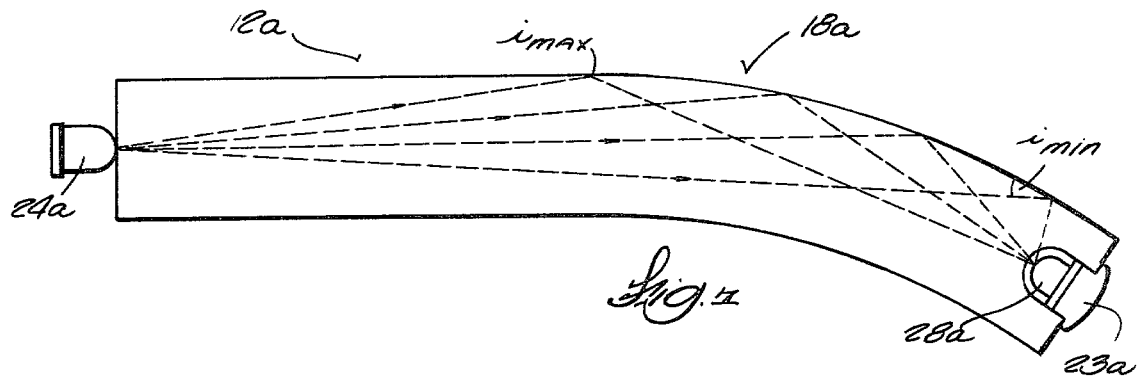
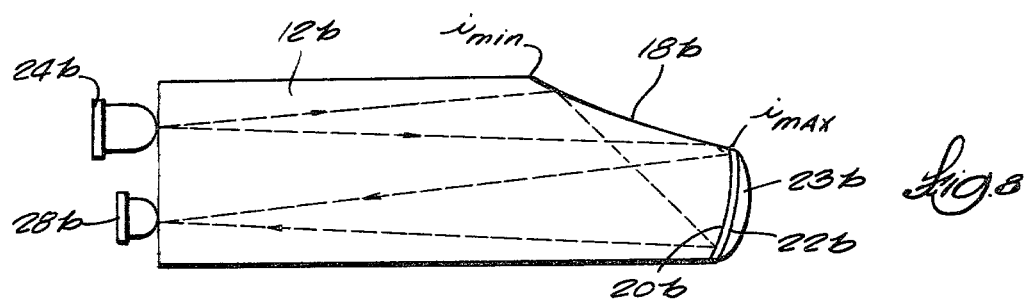
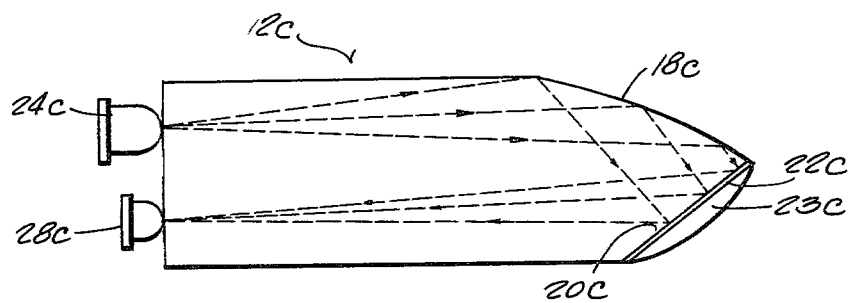

REFRACTOMETRIC DEVICE

BACKGROUND OF THE INVENTION

The invention relates to refractometric devices for measuring the concentrations of solutions and, more particularly, to immersion-type refractometric devices.

Refractometric devices which are immersed in a solution to be measured and employ the principal of internal reflection and external refraction of light are well known. In one type refractometric device, a prism having a larger refractive index than that of the solution is placed in the solution, a light source beams rays into the boundary surface between the solution and the prism, and the incident light reflected from the boundary surface is received by a photosensitive device which provides an output signal indicative of the solution concentration in response to the intensity of the reflected light. This type device usually is quite bulky, thereby limiting its field of application, and/or is expensive to manufacture. U.S. Pat. Nos. 2,780,131, 2,807,976 and 3,751,672 are representative prior art references disclosing this type refractometric device.

Another type refractometric device includes a probe having a light-transmissive, rod-like body (e.g. glass), which is immersed in the solution. The immersed end of the body has a flat active or measuring surface and one or more light reflecting surfaces coated with a light-reflective material. The unimmersed end of the probe includes a light source for directing a beam of light rays through the light-transmissive body toward the measuring surface and a light sensor for receiving light rays reflected internally through the light-transmissive body from the reflective surface and providing an output signal indicative of the solution concentration. U.S. Pat. Nos. 3,917,411, 3,932,038, 3,977,790 and 4,037,967 are representative prior art references disclosing this type refractometric device. This type device usually has one or more of the following shortcomings: (1) can measure only a narrow range of concentrations, (2) the output is non-linear over the measured range, and (3) is expensive to manufacture because the employment of means for collimating the light (either transmitted or reflected), multiple reflecting surfaces, and/or other complicating features.

SUMMARY OF THE INVENTION

A principal object of the invention is to provide a refractometric device for measuring the concentrations of solutions which is capable of providing a linear output over a relatively broad range of measured concentrations.

Another object of the invention is to provide such a refractometric device which has a simple, compact construction and can be inexpensively manufactured.

A further object of the invention is to provide a refractometric device which is capable of acting as a switch when the concentration of the solution being measured reaches a predetermined level.

Other objects, aspects and advantages of the invention will become apparent to those skilled in the art upon receiving the following detailed description, the drawings and the appended claims.

In accordance with the invention, the shortcomings of prior refractometric devices are remedied by providing the immersed tip of the light-transmissive probe with an active or measuring surface having a curved contour.

More specifically, the refractometric device provided by the invention includes a probe having a light-transmissive body with a tip on one end to be immersed in a liquid to be measured, a curved (either concave or convex) measuring surface through which light can be transmitted into the solution, a light source for emitting a diverging beam of light rays through the probe body toward the measuring surface, and a light sensing means for receiving the reflected rays and providing an output signal indicative of the solution concentration in response to the intensity of the reflected rays impinging thereon.

In one embodiment, the light sensing means includes a photosensitive element located adjacent the other (unimmersed) end of the probe and a light-reflecting surface is provided on the probe tip for receiving light rays reflected from the measuring surface and directing them through the probe body toward the photosensitive element. In another embodiment, the photosensitive element is located in the probe tip and receives reflected light directly from the measuring surface.

When a linear output over a relatively broad, predetermined range of solution concentrations is desired, the measuring surface is arranged to produce incidence angles of the reflected rays varying from a minimum corresponding to the critical angle when the solution concentration is at the lower limit of the predetermined range to a maximum corresponding to about 1.25 times the critical angle when the solution concentration is at the upper limit of the predetermined range with the rate of change of the incident angles between the minimum and maximum being substantially constant.

When a switching function is desired, the curvature of the measuring surface is contoured to provide substantially constant incidence angles across the measuring surface.

The probe body preferably is made as a one-piece unit from an elongated piece of glass. The measuring surface can be formed simply by bending the end portion of a rod of glass or other transparent, light-transmissive material to the desired curvature. When a light reflecting surface is used, a portion of the probe tip is coated with a layer of light-reflective material, preferably a vapor-deposited metal such as aluminum or the like. The layer of light-reflective material preferably is coated with a protective material which is resistent to attack by the solution.

A light emitting diode is the preferred light source because it produces less heat, requires less power and generally is more durable than incadescent lamps or the like. An intense light is desirable in order to reduce interference from ambient light by the light sensing means. When a light emitting diode which its inherently low output at rated current is used as the light source, it preferably is operated in the pulsed mode to minimize heating and yet increase the light intensity.

BRIEF DESCRIPTION OF THE DRAWING

FIG. 1 is a perspective, partially diagrammatic, view of a refractometric device embodying the invention.

FIG. 2 is a representative plot of the ratio of reflected to total light ($I/I_a$) at a point on the surface for a single light ray with probe body having a known refractive index (n), a given incidence angle (i) and a solution to be measured having a refractive index which increases with increasing solution concentration.

FIG. 3 is a family of plots similar to the plot of FIG. 2 using different incidence angles (i).

FIG. 4 is summation of the plots in FIG. 3.

FIG. 5 is a plot illustrating the curvature of the measuring surface for an exemplary probe of predetermined dimensions with the probe superimposed thereon in dashed lines to illustrate the contour of the measuring surface.

FIG. 7 is a side, partially diagrammatic, view of an alternate arrangement for the probe body.

FIG. 8 is a side, partially diagrammatic, view of another alternate arrangement for the probe body.

FIG. 9 is a side, partially diagrammatic, view of a probe capable of providing a switching function.

DESCRIPTION OF THE PREFERRED EMBODIMENTS

Figure 6:
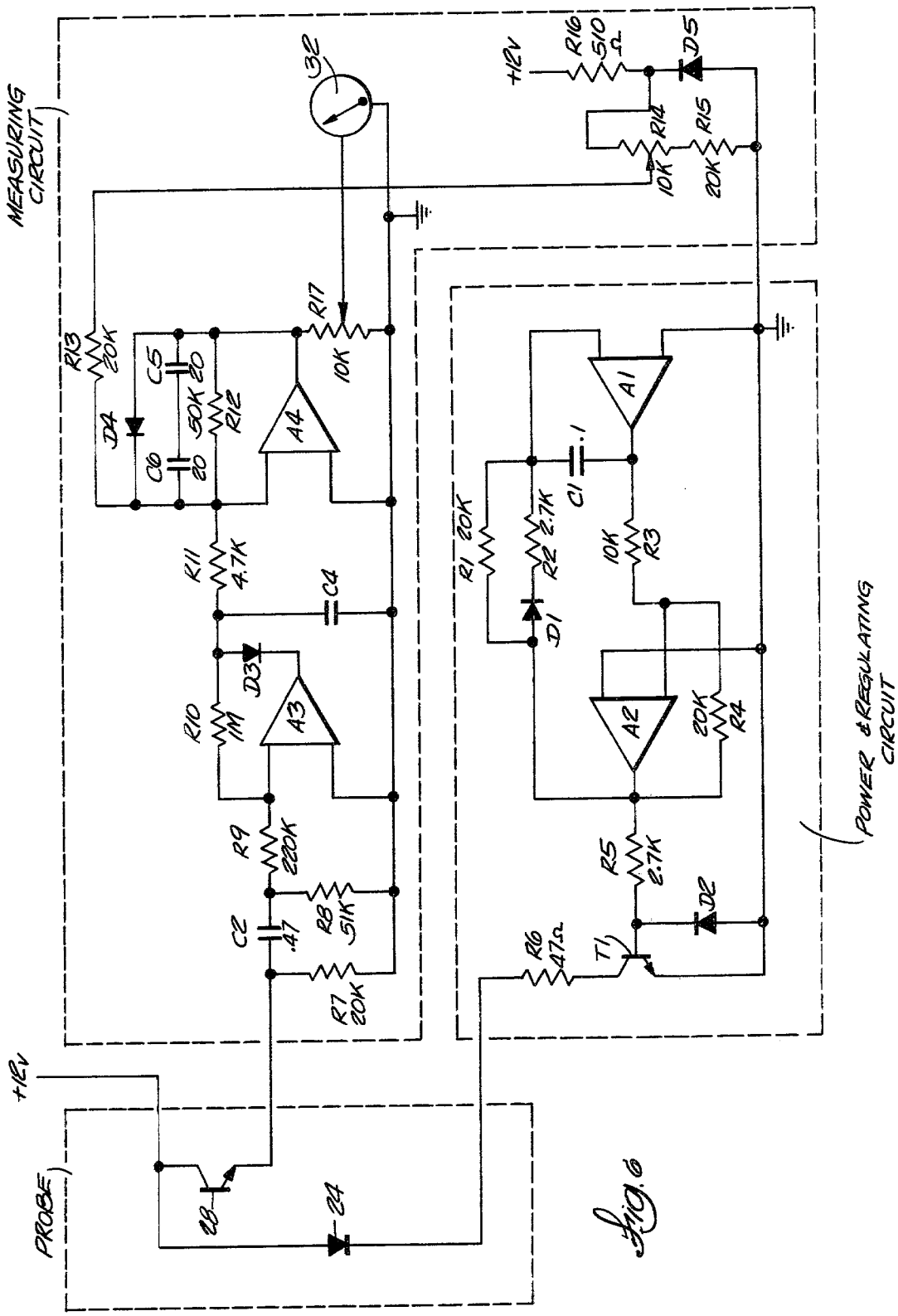
FIG. 6 is a circuit diagram illustrating a preferred measuring circuit and a preferred power and regulating circuit for the light source.

The refractometric device illustrated in FIG. 1 is designed to provide a linear output over a range of solution concentrations. It has a probe (generally designated by reference numeral 10) including a transparent or light-transmissive body 12 having a tip 14 on one end which is immersed in the solution 16 to be measured. The immersible tip 14 has a curved active or measuring surface 18 and a flat terminal surface 20 covered with a layer of light-reflective material 22. The light-reflective material 22 is encased with a protective material 23 which is resistant to chemical attack by the solution to be measured.

The probe 10 also includes a light source 24 which is suitably mounted on the unimmersed end of the probe body 12 and directs a beam of diverging light rays through the probe body toward the curved measuring surface 18. The light source 24 is electrically connected to a power and regulating circuit 26 which preferably operates the light source 24 in a pulsed mode.

The probe 10 further includes a light sensing or photosensitive element 28 which receives incident light reflected through the probe body 12 from the reflecting surface 20. The photosensitive element 28 is electrically connected to a suitable measuring circuit 30 which provides an output signal indicative of the solution concentration in response to the intensity of the incident light impinging on the photosensitive element 28. It can be appreciated that at least some of the reflected light rays may bounce off the walls of the probe body enroute from the reflecting surface 20 to the photosensitive element 28.

The output from the measuring circuit 30 can be connected to an indicating meter 32 which can be calibrated in percentage, refractive index, specific gravity or other appropriate quantitative units. If desired, the output of the measuring circuit 30 can be connected to a recording device, such as an oscillograph (not shown), or connected to an alarm and/or a control system (not shown) arranged to trigger an alarm and/or provide a control signal when the solution concentration falls below a minimum value or exceeds a maximum value.

The probe operates in accordance with the following well-known refraction equations:

$$n \sin i = n_1 \sin r \quad \text{(1) Snell's Refraction Equation}$$

and $$\frac{I}{I_o} = \frac{\sin^2(i-r)}{2\sin^2(i+r)} + \frac{\tan^2(i-r)}{2\tan^2(i+r)} \quad \text{(2) Fresnell's Equation}$$

wherein
I = light reflected from probe measuring surface
$I_o$ = light from light source striking probe measuring surface
n = refractive index of probe body
$n_1$ = refractive index of solution being measured
i = incidence angle of individual light rays
r = angle of refraction of individual light rays.

The critical angle ($i_c$), which occurs when the refractive angle of individual light rays (r) is 90° and all the light is reflected, is determined by the equation:

$$i_c = \sin^{-1} \frac{n_1}{n} \quad (3)$$

To provide a linear output the measuring surface 18 of the probe is provided with a curvature which produces angles of incidence (i) varying from a minimum ($i_{min}$) corresponding to the critical angle when the solution concentration is at a lower limit of a predetermined measurement range to a maximum ($i_{min}$) corresponding to about 1.25 times the critical angle when the solution concentration is at the upper limit of the predetermined range. As a numerical example, assume that the probe body is made from glass having a refractive index of 1.490 and the solution to be measured is an aqueous sucrose solution having a refractive index of 1.33 at 0% concentration and 1.400 at 40% concentration. For the device to provide a linear output over this range of sucrose solution concentrations, the measuring surface 18 is provided with a curved contour which produces angles of incidence varying from $\sin^{-1} 1.333/1.490$, or approximately 63.5°, to $1.25 \times \sin^{-1} 1.400/1.490$, or approximately 87.5°.

Also, the measuring surface is contoured so that adjacent incremental areas of the measuring surface 18 receive light from the light source at slightly different angles. These general criteria can be met by routine experimentation with different curvatures for particular light-transmissive probes and solutions to be measured. As a general guide, the range of linearity is smaller with smaller radii of curvature for the measuring surface 18. Furthermore, curvatures in the measuring surface must be relatively smooth in order to minimize loss of light, either transmitted or reflected.

While not completely understood at this time, the broader range of linearity provided by a probe having a curved measuring surface in accordance with the invention can be explained, at least in part, as follows with reference being made to FIGS. 2–4.

FIG. 2 is a plot of the ratio of reflected to total light at a point on the measuring surface for a single light ray (in accordance with Fresnell's equation) with a probe body having a known refractive index (n), a given incident angle (i) and a solution being measured having a refractive index ($n_1$) which increases with increasing solution concentration. As shown in FIG. 2, the amount of light reflected ($I_o$ being constant) is approximately 100% until the refractive index of the solution ($n_1$) increases to a value where the incidence angle becomes critical. The plot then drops abruptly and decreases to a point where substantially none of the light is reflected, i.e. where the reflective index of the solution ($n_1$) is about equal to the refractive index of the probe (n). This range usually corresponds to a concentration change of about 20% for an aqueous solution of sucrose. As shown in FIG. 2, the plot is not linear through this range and the usable linear portion encompasses only a small concentration change, e.g. about 3%.

The present invention is based on the premise that the sum of a finite or infinite number of curves illustrated in FIG. 2, when of the same magnitude and evenly distributed along the abscissa (the refractive index axis), produces a composite curve which has a piecewise linear central portion. This is illustrated in FIG. 3 which is a family of such curves with each representing a slightly greater incidence angle (i) of a single light ray along the measuring surface 18. The incidence angle of individual rays varies by virtue of the curvature of the measuring surface 18 as illustrated by the dashed lines in FIG. 1.

If it is assumed that each curve in FIG. 3 represents the light reflected from a point on the curved measuring surface 18 of a single probe, then the light received by the photosensitive device 28 is the sum of these rays.

FIG. 4 illustrates the summation of the curves in FIG. 3. It can be seen that the central portion of the summation curve in FIG. 4 is substantially linear. A wider linear portion can be obtained by making the diversity of incident angles (i) larger. This can be accomplished by changing the curvature of the measuring surface 18 so that adjacent incremental areas of the measuring surface receive light from a slightly different angle over a range of angles sufficient to produce a suitable linear portion over the desired range. A 0 to 40% concentration range of greater usually is required for solutions, such as aqueous solutions of sucrose and sulfuric acid, to provide the desired utility. It has been found that a probe having a flat measuring surface generally cannot provide linearity over this range of concentrations, without practical space limitations.

As further guide for determining the curvature of the probe measuring surface to provide a reasonably broad range of linearity, this curvature generally conforms to a logarithmic curve defined by the following equation $$R = Ae^{-\frac{\pi}{180}(\theta - 90 + i)\cot(\theta + 90 - i)} \quad (4)$$

wherein
R = distance from origin of light to curve
A = scaling constant
e = base of natural logarithmic
$\theta$ = rotation angle of R, degrees
i = minimum incidence angle, degrees.

FIG. 5 is a plot of a curve calculated from equation (4) using a scaling constant A corresponding to that for a probe having a predetermined length. In FIG. 5, 0 represents the origin of the light source. The shape of a representative probe of predetermined length is superimposed on the curve in FIG. 5 illustrating the contour of the measuring surface.

In the embodiment illustrated in FIG. 1, the probe body 12 is made as a one-piece unit from glass and has a rectangular cross-section. However, it should be understood that other suitable light transmissive materials, which are inert with respect to the solution being measured, can be used including chemically resistant plastic materials such as transparent acrylics, polycarbonates and the like. Also, the probe body can have suitable configurations other than the illustrated rectangular cross-section, including other polyonal, circular, or elliptical cross-sections, as long as the measuring surface meets the criteria discussed above.

While other suitable materials can be used, the light-reflective surface preferably is a vapor-deposited metal, such as aluminum or stainless steel. The surface 20 of the probe body 12 preferably should be ground or polished before depositing the metallic material 22. As mentioned above the light-reflective metallic material 22 preferably is encased with a protective material 23 which is highly resistant to attack by a variety of solutions to be measured. While other suitable materials can be used for this purpose, an epoxy type resin is preferred because of its ease of application, resistance to a wide variety of chemicals and low cost.

The light source 24 and the photosensitive element 28 are suitably mounted on the unimmersed end of the probe body 12. While other suitable light sources can be used, a conventional light emitting diode or laser diode having a built-in focusing lens and positioned to direct a diverging light beam down the longitudinal axis of the probe body 12 toward the measuring surface 18 is preferred. Such devices are less vulnerable to mechanical shock than incandescent bulbs and, without a collimating means, provide a more intensive source of light which is less susceptible to interference from ambient light.

While a phototransistor is preferred as the photosensitive elements 28, other suitable photosensitive devices, such as a photodiode, phototube, photoresistor and the like, can be used.

FIG. 6 illustrates preferred circuitry arrangements for the power and regulating circuit when a light emitting diode is used as the light source and for the measuring circuit when a phototransistor is used as the photosensitive device. The portions of the circuitry providing each function is delineated by dashed lines.

Since the amount of light reflected from the light reflective surface 20 toward the phototransistor 28 is a function of the source of intensity as well as the refractive index, a stable pulse generator is preferred. The power and regulating circuit for the light emitting diode 24 includes a pair of differential operational amplifiers A1 and A2. Amplifier A1 is an integrator by virtue of a capacitor C1 connected from the output to the inverting input. Amplifier A2 operates as a latching switch because of the positive feedback from its output to the non-inverting input provided by resistor R4. When power is applied, the integrator A1 output will be near zero. The output from amplifier A2 will be fully positive or fully negative, depending on the random noise at the instant power is applied. Assuming that the output from amplifier A2 is positive, the positive output current therefrom is driven through a diode D1 connected between the output of integrator A1 and amplifier A2 which makes resistor R1 and resistor R2 essentially parallel, resulting in a low resistance and a high charging current to capacitor C1. This causes the output of the integrator A1 to linearly increase in a rapid manner in the negative direction.

Resistor R3 connected between integrator A1 and amplifier A2 and resistor R4 connected in series between resistor R3 and the output of amplifier A2 form a voltage divider. When the negative potential of resistor R3 is approximately half the positive potential of resistor R4, the input to amplifier A2 will become negative and amplifier A2 will then switch from its full positive output to a full negative output.

In this condition, diode D1 is now back biased so that current flows only through resistor R2, capacitor C1 is slowly charged and the output of integrator A2 slowly increases in the positive direction. When the positive potential at resistor R3 increases to about half the magnitude of the negative potential at resistor R4, the input to amplifier A2 will become positive and amplifier A2 will then switch to full positive output and the cycle is repeated.

With this arrangement, the drive current to the light emitting diode 24 is pulsed at approximately 200 pulses per second with a duty cycle of approximately 10% and an amplitude of approximately 800% of the rated drive current. Thus, while the temperature rise of the light emitting diode 24 is substantially less than normal because of the pulsing input, the light intensity provided thereby is up to 8 times normal.

Still referring to FIG. 6, the measuring circuit portion includes a pair of amplifiers A3 and A4. Phototransistor 28 produces a current flow through a resistor R7, connected between phototransistor 28 and ground, when a light pulse is present. The voltage developed across resistor R7 is coupled through a capacitor C2. Any ambient light will act as a D.C. bias and is rejected by capacitor C2. Amplifier A3 amplifies and inverts the signal and diode D3 connected between the input and output of amplifier A3 clips the positive portion. Thus, amplified negative pulses flow from diode D3 to amplifier A4.

Capacitor C4 and the feedback combination of a resistor R12 and a pair of capacitors C5 and C6 connected between the input and output of amplifier A4 causes amplifier A4 to filter the pulse train. The product from resistor R12 and capacitors C5 and C6 is great enough so that the positive output approaches the peak pulse value.

Resistor R14 is the zero adjustment for the meter 32. When the probe is placed in a reference solution, such as water, resistor R14 is adjusted to cancel the input signal so that the meter reads zero. As the refractive index of the solution is increased (e.g. by dissolving a liquid or solid therein), the pulse train amplitude decreases and the output of amplifier A4 increased in the negative direction. Resistor R17 is the scaling or span adjustment for the meter 32. It is adjusted, after the meter has been zeroed, so that the meter reading agrees with the concentration of the solution.

The output from amplifier A4 can be used in a conventional alarm and/or control system to trigger an alarm and/or a control device when the solution concentration reaches a predetermined maximum and/or minimum value.

While a measuring surface having a contour approximating the logarithmic curve defined by equation (4) above produces the best linearity characteristics, it has been found that a measuring surface approximating a circular arc will produce sufficient linearity for many purposes. It should be understood that, with respect to the light source, the curved measuring surface can be either concave or convex. Alternate arrangements of the probe body having such measuring surfaces are illustrated in FIGS. 7 and 8.

In the arrangement illustrated in FIG. 7, the measuring surface 18a is concave with respect to the light source 24a. As illustrated, the diverging light rays from the light source converge after reflection from the concave measuring surface 18a. The reflected rays strike a photosensitive element 28a suitably mounted in the outer end portion of the probe body 12a. With this arrangement, there is no need for a light-reflecting surface. However, the probe can be arranged in the manner illustrated in FIG. 1 if desired. It should be noted that the minimum incidence angle ($i_{min}$), corresponding to the critical angle of the lower end of the desired concentration range, is furthest from the light source and the incidence angles increase in a direction along the measuring surface toward the light source.

In the arrangement illustrated in FIG. 8, the measuring surface 18b is convex with respect to the light source 24b. The diverging light rays from the light source diverge even more after being reflected from the convex measuring surface. Consequently, it is not feasible to mount the photosensitive element 28b on the probe tip as illustrated in FIG. 7. Instead, the photosensitive element 28b is mounted on the other end and a concave light-reflecting surface 20b is provided to focus the reflected rays onto the photosensitive element 28b. It should be noted that the positions of the minimum and maximum incidence angles for the convex measuring surface are reversed from those for a concave measuring surface, i.e. the minimum incidence angle ($i_{min}$) is closest to the light source.

It is obvious that the curvature of the measuring surface can be varied in either arrangement to increase or decrease the variation of incidence angles seen by the diverging light rays to thereby vary the measuring range of the probe.

The device illustrated in FIG. 9 is designed to provide a switching function when a solution concentration reaches a predetermined level. The concave measuring surface 18c is contoured so that the incidence angles of the diverging light rays are approximately equal across the measuring surface. The light-reflecting surface 20c is flat and preferably at 90° to the central reflected ray. With this arrangement, the light reflected from the light-reflecting surface 20c converges in approximately the same vertical plane as the light source. Thus, it is advantageous to locate the photosensitive element 28c next to the light source 24c at the convergence point.

Since there is no diversity of incidence angles at the measuring surface 13c, the measuring range is minimum and the ratio of reflected to total light characteristic resembles that illustrated in FIG. 2. Thus, the output changes quite abruptly when the refractive index of the solution being measured passes through the critical point. This abrupt change in output can be conveniently used to provide a switching function.

From the foregoing description, one skilled in the art can easily ascertain the essential characteristics of the invention and, without departing from the spirit and scope thereof, can make various changes and modifications to adapt it to various usages and conditions.

I claim:

1. A refractometric device for measuring the concentration of solutions and providing a substantially linear output over a predetermined range of solution concentrations, said device including
   a probe having a light-transmissive body including a portion to be immersed in the liquid to be measured and having an outermost end;
   a curved measuring surface on said immersible portion inwardly from said outermost end through which light can be transmitted into the solution and from which light rays are reflected when said immersible portion is immersed in a liquid, the curvature of said measuring surface being contoured to provide incidence angles of the reflected light rays varying from a minimum corresponding to the critical angle when the solution concentration is at the lower limit of the predetermined range to a maximum corresponding to about 1.25 times the critical angle when the solution concentration is at upper limit of the predetermined range;

a light source for emitting a diverging beam of light rays through the probe body toward the measuring surface; and light sensing means for receiving light rays reflected from said measuring surface and providing an output signal indicative of the solution concentration in response to the intensity of the reflected light rays impinging thereon.

2. A refractometric device according to claim 1 wherein said measuring surface is concave with respect to said light source.

3. A refractometric device according to claim 2 wherein said light sensing means includes a photosensitive element located adjacent the end of said probe body opposite to said outermost end; and said probe body includes a light reflecting surface on said outermost end for receiving light rays reflected from said measuring surface and directing them through said probe body toward said photosensitive element.

4. A refractometric device according to claim 3 wherein said light reflecting surface is substantially flat.

5. A refractometric device according to claim 3 wherein said light sensing means includes a photosensitive element mounted on said outermost end for directly receiving light rays reflected from said measuring surface.

6. A refractometric device according to claim 1 wherein said measuring surface is convex with respect to said light source.

7. A refractometric device according to claim 6 wherein said light sensing means includes a photosensitive element located adjacent the end of said probe body opposite to said outermost end; and said probe body includes a light reflecting surface on said outermost end for receiving light rays reflected said measuring surface and directing them through said probe body toward said photosensitive element, said light reflecting surface being concave with respect to said light source.

* * * * *